United States Patent [19]

McNeil et al.

[11] Patent Number: 4,830,959
[45] Date of Patent: May 16, 1989

[54] ELECTROCHEMICAL ENZYMIC ASSAY PROCEDURES

[75] Inventors: Calum J. McNeil, Glasgow, Scotland; Joseph V. Bannister, Oxford, Great Britain

[73] Assignee: Medisense, Inc., Cambridge, Mass.

[21] Appl. No.: 929,332

[22] Filed: Nov. 10, 1986

[30] Foreign Application Priority Data

Nov. 11, 1985 [GB] United Kingdom ............... 8527777
Aug. 5, 1986 [GB] United Kingdom ............... 8619113

[51] Int. Cl.[4] ..................... G01N 33/53; C12Q 1/42
[52] U.S. Cl. ............................... 435/7; 435/21; 435/810; 435/817; 436/501; 436/518; 436/537; 436/806; 436/904; 204/403
[58] Field of Search ............ 435/7, 810, 817, 21, 435/18, 19; 436/501, 518, 537, 806, 904; 204/403

[56] References Cited

U.S. PATENT DOCUMENTS 4,595,655 6/1986 Self ........................... 436/537 X

FOREIGN PATENT DOCUMENTS 0125867 11/1984 European Pat. Off. ............ 435/4
0125139 11/1984 European Pat. Off. ............ 435/6
2173313 10/1986 United Kingdom .
8502627 6/1985 World Int. Prop. O. .

Primary Examiner—Robert J. Warden
Assistant Examiner—Jack Spiegel

[57] ABSTRACT

Electrochemical detection of mediator level is employed in a method of assay using a redox enzyme and redox substrate to detect conversion to an effective mediator by an assay enzyme label of a compound which is non-mediating under the assay conditions.

17 Claims, 3 Drawing Sheets

ELECTROCHEMICAL ENZYMIC ASSAY PROCEDURES

This invention relates to electrochemical enzymic assay procedures.

More particularly, but not exclusively, the present invention relates to techniques and equipment useful in immunoassays. The invention is especially concerned with immunoassays of use for instance in a wide range of diagnostic or investigative techniques for humans or animals, or for example in investigating and monitoring of food chemistry or process chemistry.

An example of a known enzyme-labelled assay is the heterogeneous immunoassay known as the ELISA (enzyme-labelled immunosorbent assay) technique. In the commonly adopted ELISA sandwich procedure, the technique will typically involve three steps, separated by washes and rinses:

(a) immobilisation of a suitable antibody on a support surface, such as polymer beads or possibly the walls of a plastics vessel or recesses in a plastics dish;

(b) contacting the surface carrying immobilised antibody with the sample to be investigated, whereby a specific analyte in the sample can bind to the antibody in a proportion dependent on the analyte concentration; and (c) further contacting the surface with an antibody labelled with an enzyme, this enzyme-labelled antibody binding only to the antigen and thus providing at the surface the enzyme in a measurable concentration corresponding to the analyte concentration in the sample.

The sandwich technique has certain limitations, most especially in that it can only be used with analyte molecules having at least two epitopes, so as to react both with the immobilised antibody and with the enzyme-labelled antibody.

In the alternative ELISA competitive procedure for assay of a specific analyte, a known concentration of enzyme-labelled specific analyte is added to a sample which is then contacted with a surface supporting an known concentration of antibody, whereby labelled and unlabelled analyte compete proportionally for binding sites, and a subsequent measurement of enzyme concentration will indicate the labelled/unlabelled ratio.

Most of the existing ELISA and other enzymic assay procedures use a colour-forming substrate which at the end of the incubation releases a chromophore whose concentration can be determined spectrophotometrically. The use of colour-forming substrates may have their drawbacks in view of the length of time required to obtain a result and also the instability of some chromophores. Thus there is a need for an improved assay procedure.

As an alternative to colour detection, an instance of electrochemical detection is described in Anal. Chem. (1984) 56, 2355, where the assay enzyme label converts an electroinactive compound to an electroactive compound which can be electrochemically detected. The electroactive compound, phenol, has a redox potential of +750 mV, and as such the method is not generally applicable because the system will encounter other components which will oxidise at the potential of 750 mV. In practice, this system therefore can not be adopted with a blood or serum sample.

The present invention especially relates to assay techniques utilising amplification of a response, particularly for detecting the presence of or monitoring the level of one or more substances in a mixture of components, where the analyte is present in particularly low concentration and/or in admixture with potentially interfering substances, and wherein the presence or absence of the response is linked to the extent of a specific binding reaction.

European Patent Specification No. 78636 describes the use of a mediator compound such as a ferrocene derivative to transfer electrons between an enzyme and an electrode when the enzyme catalyses a redox reaction on a substrate. Such a procedure is of major utility for electrochemical detection of glucose as substrate by adoption of a glucose oxidase as the redox enzyme.

In more recent European Patent Specifications such as EP125139, assays are described in which the concentration of substrate is fixed, and the concentration of available mediator compound represents the variable factor. In this way, the procedure of EP78636 is inverted, and the combination of the redox enzyme and substrate allows electrochemical detection of the mediator.

The present invention is concerned with a further development of assays based on electrochemical detection of mediator levels using a redox enzyme and substrate.

OBJECTS OF THE INVENTION

A principal object of the present invention is the provision of improved enzyme-labelled assays. More specifically, a particular object of the present invention is an improved ELISA technique. Other objects include reagents for novel enzyme-labelled assays.

SUMMARY OF THE INVENTION

The present invention provides for the use of electrochemical detection of mediator level using a redox enzyme and redox substrate to detect conversion in an assay of a non-mediating compound to an effective mediator by an assay enzyme label.

Thus, the present invention employs electrochemical procedures for detecting the effective mediator generated from a compound which is not a mediator under the assay conditions. The effective mediator is generated by an enzyme used as label in an assay. In turn, this allows the determination of an analyte in a qualitatative or quantitative sense. A relatively sensitive and fast immunoassay in the nanomolar range can be achieved.

The conditions are selected so that a substrate for the assay enzyme label is not effective as a mediator, and the action of the assay enzyme label converts the substrate to an effective mediator. The non-mediating compound may itself be a potential mediator, except that under the selected conditions the compound is not effective as a mediator, and is thus "non-mediating".

In this way, there is provided a method of assay in which an enzyme label is employed, characterized in that the label is electrochemically detected with a redox enzyme and a redox substrate as a result of conversion by the labelling enzyme of a non-mediating substrate from an ineffective mediator to an effective mediator for mediating electron transfer between the redox enzyme and an electrode.

The use of assay enzyme labels together with a mediator/redox enzyme system facilitates the extension of known specific binding assays to finer levels of resolution than those previously accomplished, without the requirement for pretreatment of samples to remove interfering substances.

The present system is distinguished from that described in the patent specification of PCT/GB 8600095 in that the redox substrate for the present invention is freely diffusing before conversion into the effective mediator, whereas in the prior system, the potentially active component is inactivated by linkage to a relatively large molecule of an immobiliser material.

PREFERRED EMBODIMENTS OF THE INVENTION

The assay of this invention is typically an immunoassay. The assay suitably involves a sandwich or competitive procedure. Thus, in a preferred aspect, the assay of this invention is a sandwich ELISA or a competitive ELISA.

For a sandwich assay, a mono- or polyclonal antibody is immobilized, the sample is contacted with the immobilized antibody, enzyme-labelled antibody is then contacted with the system, the substrate is added with the system conditions being such that the substrate is non-mediating, and then the electrochemical determination of the effective mediator is carried out with the redox enzyme and the redox substrate.

For a competitive assay, the sample and an enzyme-labelled analyte are contacted with immobilized antibody, the non-mediating substrate is added, and the electrochemical determination is effected.

Generally, in the electrochemical detection, the non-mediating substrate will preferably itself be a potential mediator rendered non-mediating because of the operating conditions. To this end, an electrode is poised at a preselected potential which is intermediate between the redox potential of the substrate for the redox enzyme and the product, such that only the product having a redox potential lower than that at which the electrode is poised can undergo a redox reaction at the electrode.

By employing the product has a mediator which exhibits electron transfer at a preselected potential, and which can be formed by an enzyme reaction from a substrate which exhibits no mediator activity at the preselected potential, it is possible to determine the extent of conversion of the substrate into the product and consequently the presence or activity of the enzyme. It will be realised that a variety of assay protocols may be envisaged, in which the conversion of the substrate into the product is accompanied by an increase of mediator activity under the conditions of the assay.

The substrate for the labelling enzyme is a mediator derivative which is non-mediating under the assay conditions. The nature of the derivative will depend on the nature of the labelling enzyme.

Examples of mediator compounds which can form the basis of the substrate include metallocenes; ruthenium compounds; carboranes; conductive salts of tetracyanoquinodimethane (TCNQ); haloanils and derivatives thereof; viologens; quinones; alkyl substituted phenazine derivatives; bis-cyclo pentadienyl $(Cp)_2MX_x$ complexes of transition metals; and phenol derivatives including ferrocene-phenol and indophenol compounds. Such compounds are readily derivatised to provide suitable substrates.

By the use of water-soluble, air-insensitive derivatives it is possible that the assay may be performed in samples of biological fluids which have undergone a minimum of pretreatment.

Suitable derivatives which provide the substrate for a given enzyme can readily be synthesised. For example, phosphate derivatives are recognised by acid or alkaline phosphatases.

Conveniently, the substrate for a phosphatase labelling enzyme is a metallocene derivative, preferably a ferrocene derivative.

Examples of suitable phosphate derivatives of ferrocene are:

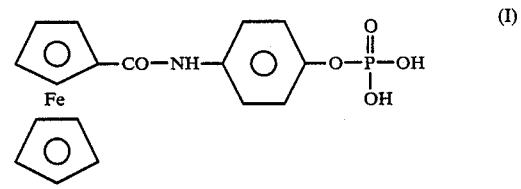

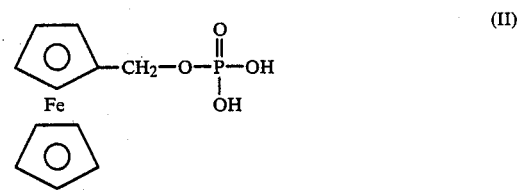

In a particularly preferred embodiment of the present invention, the redox substrate is the phosphate compound (I), otherwise termed,

and herein called [N-ferrocenoyl]-4-aminophenyl phosphate. This compound is a novel compound and also forms part of the present invention.

The compound [N-ferrocenoyl]-4-aminophenyl phosphate has an $E_{\frac{1}{2}}$ of $+390$ mV against a standard calomel electrode ("SCE"). When the compound is treated with a phosphatase, such as acid or alkaline phosphatase, it is converted into the phenol derivative;

which has an oxidation potential of $+180$ mV against SCE. Hence, when an amperometric measurement is made at about $+230$ mV against SCE, only the catalytic current due to compound (A) is detected, and the compound (I) shows no electrode response at this potential.

In one alternative preferred embodiment, the substrate is a phenol derivative such as 2,6-dichloroindophenyl phosphate, which is of the formula (III)

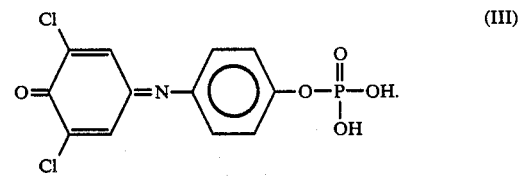

Although phosphatases are particularly exemplified, the the invention is applicable to any enzyme substrate coupled to any electroactive species. Therefore, this invention is not limited to such phosphate compounds for use with a phosphatase as labelling enzyme. Mediator derivatives can readily be synthesised so as to be coupled to other enzymic systems, and accordingly the nature of the reaction catalysed by the assay enzyme label is not critical. For example, the enzyme can be a protease, amidase or hydrolase.

According to another aspect of the present invention there is provided a system for detecting the activity of a first enzyme, comprising:

(a) a freely diffusing reagent convertible by the first enzyme into a product exhibiting mediator activity thereby enabling detection of the product, and, (b) detection means comprising a redox enzyme, a substrate for the redox enzyme, and an electrode, whereby, in the presence of an active form of the first enzyme, the reagent is converted into the product and a detectable change occurs in mediated electron transfer to the electrode. Typically, the characteristic mediator property of the product is electron transfer at a preselected electrode potential.

Such a system can be used to provide an assay for the first enzyme, whether or not the first enzyme is a label.

In another aspect of the present invention there is provided a bioelectrochemical cell (BEC) incorporating a substrate for an assay enzyme label whereby consumption of the substrate by said assay enzyme label produces a change in output from the BEC enabling said enzyme to be detected. The BEC comprises a second enzymic reaction system which provides the electrical output through conversion of the substrate to a mediator.

For the second enzymic reaction used in the BEC, a ferrocene mediator is preferred for mediating electron transfer in the reaction between glucose and glucose oxidase. Such a system results in amplification of the effect of the redox potential change in the ferrocene compound, owing to the mediator action of the ferrocene compound. The chemical change in the ferrocene compound or other substrate as it is consumed by the enzyme analyte can have a marked effect on the mediator characteristics, and hence on the output from the BEC.

According to a yet further aspect of the invention there is provided a method for detecting the activity of a non-redox enzyme, in the presence at least one electrode poised at a fixed potential, which method comprises;

(a) treating a sample suspected of containing the non-redox enzyme with a reagent which has a redox potential higher than the poised potential of the electrode, the reagent being a substrate for the non-redox enzyme, and convertible by the activity of the non-redox enzyme into a product which acts as a mediator compound and has a redox potential lower than the poised potential of the electrode, and, (b) treating the sample with a redox enzyme, and a substrate for the redox enzyme whereby in the presence of a mediator compound having a redox potential lower than the poised potential of the electrode, a measurable transfer of charge to the electrode occurs.

The present invention enables the detection of the activity of enzymes which do not themselves exhibit redox activity but which in one aspect of the invention can catalyse the transformation of a substrate in to a product which has mediator properties under the conditions of assay.

It should be noted that while the invention will be described hereafter with reference to a phosphatase enzyme, the invention extends to other assay systems and to other reagents. For example, it is envisaged that other labelling enzymes may be employed, each being capable of reacting with a reagent to produce a product which has mediator properties. Moreover, while the invention is described with reference to the labeling of antigens, it is envisaged that enzyme labels in other types of specific binding reactions, such as those between complementary strands of nucleic acid, may be employed.

SUMMARY OF THE DRAWINGS

In FIG. 1, mediator compound ($M_i$) is for example the compound (I). This compound is a water soluble reagent which with an electrode poised at a potential of +230 mV against SCE exhibits no mediator activity between glucose oxidase (GOD) and its substrate glucose.

In the presence of phosphatase enzyme (E) present as a label, the compound (I) is converted into the compound (A), which does exhibit mediator activity ($M_{red/ox}$) between glucose oxidase (GOD), its substrate glucose, and an electrode poised at +230 mV against SCE.

Figure 1:
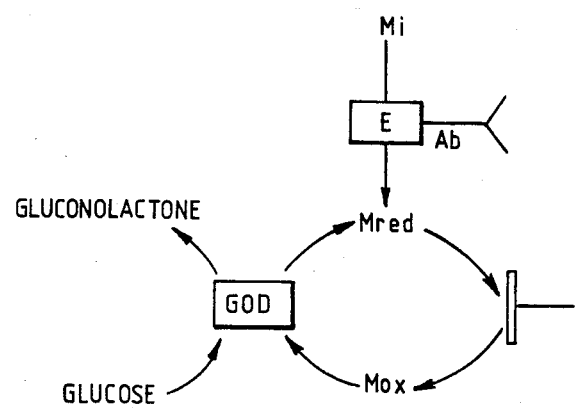
FIG. 1 is a general scheme for an assay of the present invention.

Thus, the system of FIG. 1 enables the detection of the activity of the phosphatase enzyme. The detected current at the electrode is due only to the presence of compound (A).

In FIG. 1, the phosphatase enzyme is a label for the antibody (Ab), and consequently the concentration of the phosphatase enzyme is affected by specific binding reactions between the antibody and its corresponding antigen. The steps of exposing the antibody to the antigen and separating bound and free fractions may be carried out in accordance with known techniques of immunoassay. In a variation, the phosphatase enzyme can be a label for the antigen.

SPECIFIC EXAMPLES OF THE INVENTION

In order that the invention may be better understood and carried into effect, various embodiments given by way of non-limiting example will now be described with reference, where appropriate, to the accompanying drawings.

EXAMPLE 1

Preparation of a Substrate, Compound (I)

(a) Preparation of Compound (A):

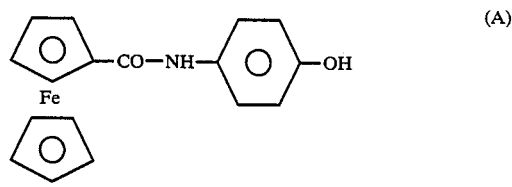

(A)

Ferrocene monocarboxylic acid was converted to the ferrocenoyl chloride by the method described in J. Org. Chem., 24, 280–281, (1959).

Ferrocenoyl chloride (1 mM) was then dissolved in 5 ml of ice-cold dry pyridine. To this solution was added in one portion a solution of p-aminophenol (1.1 mM) in 5 ml dry pyridine. The reaction was allowed to proceed for 2 hours at 4° C. and then the solution was warmed to room temperature and stirred for a further 2 hours. After this time the solution was filtered and the solvent removed in vacuo. The residue was then dissolved in the minimum amount of ethyl acetate and the compound purified by column chromatography on silica using ethyl acetate/hexane (3:1 v/v) as the eluent. The purified compound was crystallised as orange needles by slow diffusion of hexane into a solution of the compound in a minimum amount of ethyl acetate Mass spectroscopy gave a parent ion peak at m/e=321, corresponding to the desired compound (A).

(b) Preparation of Compound I:

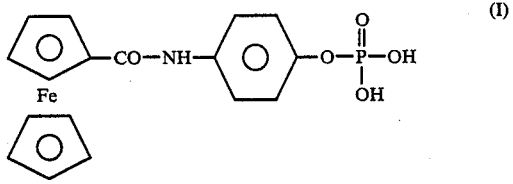

The substrate for the alkaline phosphatase assay was prepared by modification of the methods in Biochem. J., 47, 93–95, (1950) and Biochem. J., 33, 1182–1184, (1939).

Compound (A) (100 mg, 0.31 mM) was dissolved in 5 ml of dry pyridine, and the mixture cooled in an ice bath. To this solution was added freshly distilled phosphorous oxychloride (30 μl, 0.32 mM) and the resulting mixture stirred at 0° C. until the reaction was complete. The reaction was followed by tlc using ethyl acetate as eluent.

Once the reaction was complete, a small amount of water (about 5 ml) was added and thereafter saturated barium hydroxide was added at 0° C. until the solution was alkaline. After the addition of barium hydroxide, an equal volume of ice-cold ethanol was added to precipitate the barium salt of the phosphoric ester. The barium salt was collected by filtration, washed with ethanol and dried in vacuo.

The crude barium salt was only slightly soluble in water. It was treated with a stoichiometric amount of $H_2SO_4$. The solution was filtered and subsequently lyophilised to yield the free acid.

EXAMPLE 2

Preparation of an alternative substrate, Compound (II)

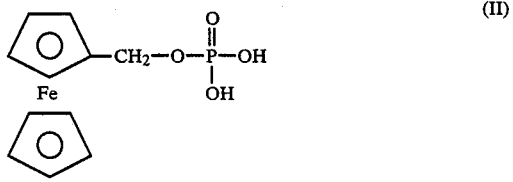

Hydroxymethyl ferrocene (216 mg) was dissolved in 5 ml of dry pyridine and thereafter 111 μl of fresh phosphorus oxychloride was added in one portion. The clear yellow solution immediately turned dark red, and hydrogen chloride gas was released. The solution was stirred for approximately two hours. The reaction of hydroxymethyl ferrocene was confirmed by tlc on silica plates using ethyl acetate as eluent. After five minutes reaction, no hydroxymethyl ferrocene could be detected in the mixture.

After two hours, 10 ml of slightly basic distilled water (pH around 8) was added to the solution, which was then extracted four times with ethyl acetate to remove pyridine. The aqueous layer was further extracted four times with chloroform and then evaporated to dryness on a rotary evaporator. The residue was taken up four times in slightly acidic distilled water (pH 5.5) and repeatedly evaporated to dryness in order to remove any residual pyridine.

The product was dissolved in ethanol in order to precipitate any inorganic impurities which were then filtered off.

Finally, in order to dry the product, it was dissolved in a minimum amount of distilled water and then freeze-dried for forty-eight hours.

A crystalline material, compound (II), was obtained upon standing at 4° C. for forty-eight hours.

EXAMPLE 3

Determination of redox potentials

The redox potentials of compound (I) and compound (II) were determined.

An electrochemical cell was set up using a gold working electrode, a saturated calomel reference electrode (SCE) and a platinum counter electrode, connected to a potentiostat. The clean electrochemical cell was filled with a solution of the ferrocene derivative (2 mM) and glucose (80 mM) in 100 mM Tris at pH 10.15. The final volume was 400 μl. Two different buffers were used to make up the solution, but did not affect the results.

The voltage was swept from 0 to 600 mV at a rate of 5 mVsec$^{-1}$. From the resultant voltammograms, the redox potentials of compounds (I) and (II) were calculated.

For compound (I), the redox potential is around +390 mV.

For compound (II), the redox potential is around +370 mV.

The redox potential of compounds (I) and (II) were pH-independent in the range studied.

EXAMPLE 4

Preparation of an alternative substrate, Compound (III)

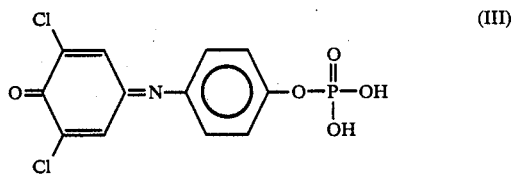

5 g of the sodium salt of 2,6-dichloroindophenol was dissolved in water and hydrogen chloride gas was added until a deep blue precipitate was deposited. The solid was filtered, dissolved in dichloromethane and dried over magnesium sulphate. The solution was filtered and the solvent removed to yield 2,6-dichloroindophenol.

The 2,6-dichloroindophenol was dissolved in dry pyridine and one equivalent of phosphorus oxychloride was added dropwise with stirring. After 15 minutes, ice was added and the solution neutralized with sodium carbonate. The solvent was removed and the residue extracted with boiling ethanol. The ethanol was filtered and evaporated. The residue was washed with ethanol to yield the desired compound (III).

EXAMPLE 5

Determination of Alkaline Phosphatase Activity

A two compartment electrochemical cell was used. In addition to a 4 mm diameter graphite disc working electrode, the cell contained a 1 cm² platinum gauze counter electrode and a saturated calomel electrode ("SCE") as a reference.

D.C. cyclic voltammetry experiments were carried out using a BAS-100 Electrochemical Analyser.

Calf intestine alkaline phosphatase (supplied by Calzyme) was dialysed into 0.1M Tris buffer, pH 10.15. The final protein concentration was 0.86 mg/ml. 0.6 ml of a 2 mM substrate solution in 0.1M Tris pH 10.15, containing 10 mM $MgCl_2$ and 50 mM NaCl, was placed in the sample compartment of the electrochemical cell and the D.C. cyclic voltammogram recorded. The peak current, if any, at 180 mV was measured and thereafter, 100 $\mu$l of a suitably diluted stock solution of alkaline phosphatase was added and the cell contents incubated at room temperature for 15 minutes. After incubation the cyclic voltammogram was again recorded and the current at 180 mV measiured. This procedure was repeated for a range of alkaline phosphatase concentrations.

Figure 2:
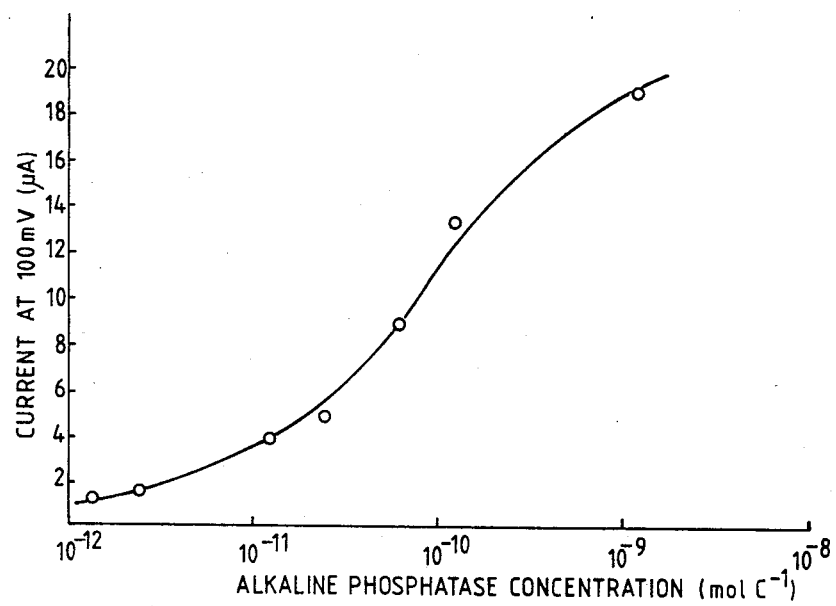
FIG. 2 is a plot of peak current at 180 mV against phosphatase concentration, obtained in Example 5.

The peak current at 180 mV due to the oxidation of ferrocene to the ferricinium ion in the phenolic product was used to estimate alkaline phosphatase activity. The peak currents at 180 mV as a function of alkaline phosphatase concentration are shown graphically in FIG. 2.

An in-cell concentration of $1.23 \times 10^{-12}$ mol $l^{-1}$ alkaline phosphatase is equivalent to $8.6 \times 10^{-16}$ moles of enzyme in the electrochemical cell. Accordingly, a very low amount of alkaline phosphatase can be determined using cyclic voltammetry under relatively mild conditions, with 15 minutes incubation at room temperature (as opposed to the more common conditions used in immunoassays, with at least 30 minutes incubation at 37° C.).

EXAMPLE 6

Amperometric ENDAB Enzyme Immunoassay

Having demonstrated the inherent sensitivity of the electrochemical alkaline phosphatase assay, a detection system for enzyme immunoassay was tried. An ENDAB enzyme immunoassay kit for unconjugated oestriol in serum was purchased from CMD (UK) Ltd.

The assay procedure supplied with the oestriol kit was followed until the second antibody precipitation step, and then modified to give an assay of this invention. Thus, 50 $\mu$l of each oestriol standard (0, 1, 3, 10, 20 and 40 ng ml$^{-1}$) were pipetted into the appropriate glass tubes. In order to allow for non-specific binding ("NSB"), 50 $\mu$l of the 0 ng ml$^{-1}$ standard was placed in the NSB tube. Thereafter, 25 $\mu$l of the oestriol-enzyme conjugate was added to all the tubes, followed by 100 $\mu$l of oestriol anti-serum. Oestriol anti-serum was not added to the NSB tube, and instead 100 $\mu$l of Background Reagent was added.

The reagents were mixed and incubated for 20 minutes at room temperature. 1 ml of the second antibody-separating reagent was then added to all tubes. The tubes were centrifuged at 3000 rpm for 10 minutes and the supernatant discarded. The tubes were then blotted on absorbent paper to remove excess liquid.

At this point, instead of following the procedure specified with the kit for spectrophotometric determination of oestriol, the centrifugal pellet, which contained the antibody-found oestriol-alkaline phosphatase, was resuspended in a solution containing the ferrocene linked substrate (0.6 ml of a 2 mM solution in 0.1M Tris, pH 10.15 containing 10 mM $MgCl_2$ and 50 mM NaCl). The solution was incubated at room temperature for 15 minutes. After 15 minutes incubation, the solution was transferred to the sample compartment of the electrochemical cell.

The cyclic voltammogram of the solution was recorded over the range 0 to +650 mV versus SCE, and the peak current at 180 mV measured.

This procedure ws carried out for each serum oestriol standard, that is, 0, 1, 3, 20 and 40 ng/ml.

The background current at 180 mV for the substrate in the absence of any alkaline phosphatase, that is, the non-specific binding current, was 1.15 $\mu$A. This value was subtracted from the results obtained using the serum standards.

Figure 3:
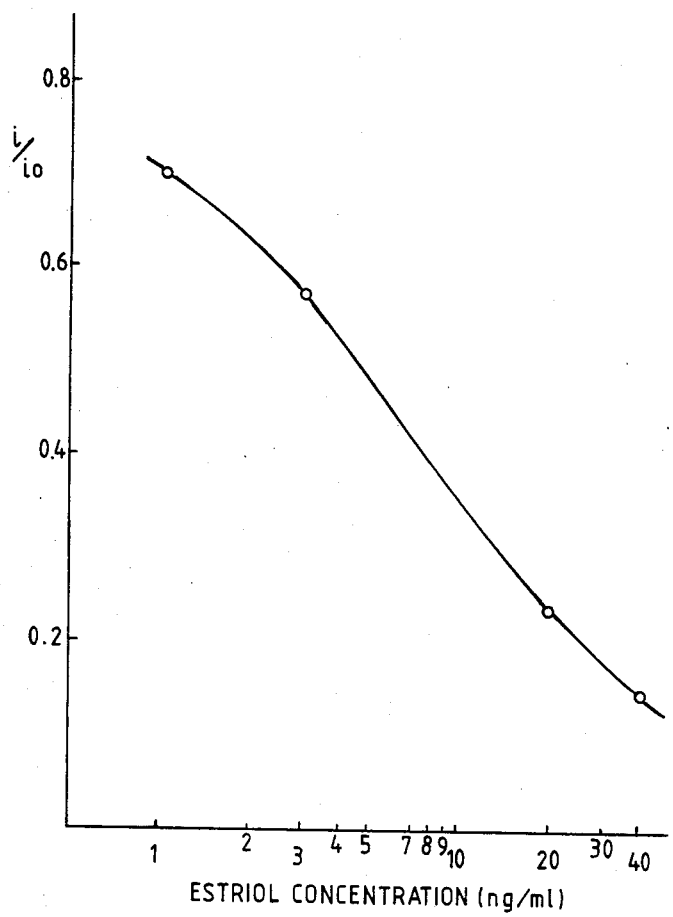
FIG. 3 is a plot of corrected peak current at 180 mV against oestriol concentration for a set of serum standards in the assay of Example 6.

The corrected peak current at 180 mV for each serum standard was plotted on the standard-curve paper supplied with the kit to give FIG. 3.

Plotting—ln $i/i_o$ against oestriol concentration gave a straight line (y=0.04x+0.43, r=0.98).

This ENDAB immunoassay with amperometric detection was achieved using shorter incubation times and lower temperatures than the standard kit method.

EXAMPLE 7

(a) Use of compounds (I) and (II)

The same apparatus and voltage sweep was used as in Example 3.

In this experiment 1 $\mu$l of the enzyme glucose oxidase (GOD), 175 mg/ml, was added to the solutions as in Example 3, giving a final volume of 0.35 ml.

The voltage sweep was carried out as before and the results, current against voltage, were recorded.

It was found that both compounds (I) and (II) will act as mediators for the glucose oxidase enzymic reaction and that the resulting current produced at oxidising potentials had been amplified. This amplification is due to the catalytic reduction of the ferricinium ion by the enzyme and the subsequent reoxidation of ferrocene at the electrode.

Measurements against time of current at a constant potential of 450 mV were performed in the three-electrode system, with detection of hydrolysis of the phosphate group of the ferrocene derivative in the presence of a crude preparation of an acid phosphatase. 8 $\mu$l compound (II) (50 $\mu$M in ethanol) and 50 $\mu$l glucose (1M) in 100 mM citrate buffer, pH 4.66, were used, giving a final volume of 400 $\mu$l. The samples were all stirred throughout the experiment.

Four sets of measurements were recorded:

(a) Compound (II) plus glucose, no acid phosphatase or glucose oxidase.

(b) As (a) but with the addition of 25 $\mu$l of 2 mM glucose oxidase after ten minutes incubation of compound (II) and glucose at 37° C. The incubation was used to show that any decrease in current occurring after addition of acid phosphatase was not due to breakdown in solution of compound (II).

There was a clear difference in current between (a) and (b), due to the oxidase enzymic reaction acting through compound (II) as a mediator.

(c) As (b) but with 10 $\mu$l of crude acid phosphatase solution incubated with compound (II) and glucose for ten minutes at 37° C. prior to addition of glucose oxidase.

A decrease in current compared with (b) was observed, presumably due to reaction of acid phosphatase on compound (II), which alters its mediator characteristics.

(d) As (c), but 30 μl of acid phosphatase solution was added.

A further decrease in current was observed, showing an inverse relationship between the acid phosphatase concentration and the catalytic current.

(b) Use of compound (III)

Figure 4A:
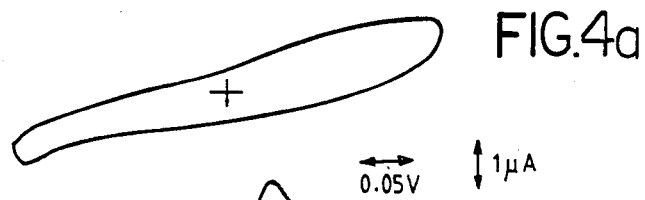
FIG. 4 comprises a set of cyclic voltammograms obtained in Example 7(b).
Figure 4B:
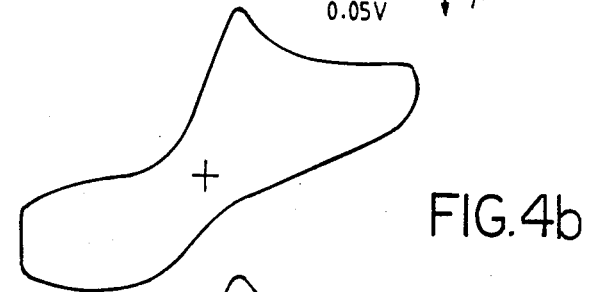
Figure 4C:
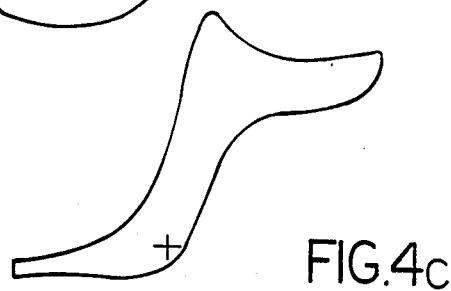

In a similar manner to Example 7(a), the cyclic voltammogram of compound (II) with 0.1M glucose was determined at pH 7.8 using a scan rate of 20 mV/s, giving curves (a), (b) and (c) of FIG. 4 respectively for the compound (III), the compound (III) after 5 minutes with alkaline phosphatase, and the compound (III) with alkaline phosphatase and glucose oxidase. Again the amplification was marked.

We claim:

1. A method of assaying for activity of a first enzyme able to convert a non-mediator to a mediator, said mediator having a reduced form and an oxidized form, said method comprising:
   (a) providing a sample to be assayed for said activity of said first enzyme;
   (b) contacting said sample with freely circulating non-mediator;
   (c) providing a second enzyme, said second enzyme being catalytically active in the absence of said mediator;
   (d) providing a substrate for said second enzyme;
   (e) providing an electrode at an electrical potential which is intermediate between the redox potential of said mediator and said non-mediator, said mediator being capable of transferring charge between said second enzyme and said electrode, said electrical potential is such that said mediator is converted from said reduced form to said oxidized form at said electrode and said non-mediator is not oxidized or reduced at said electrode;
   (f) measuring the current generated at said electrode, said current providing a measure of the conversion of said non-mediator to said mediator; and
   (g) correlating the current generated at said electrode with the presence of said first enzyme.

2. The method of claim 1 wherein said first enzyme is a label for an antibody or an antigen.

3. The method of claim 2, wherein said immunoassay is an ELISA.

4. The method of claim 1, 2, or 3 wherein said mediator is selected from the group consisting of: metallocenes, ruthenium compounds, carboranes, conductive salts of tetracyanoquinodimethane (TCNQ), haloanils, viologens, quinones, alkyl-substituted phenazines, and bis-cyclo pentadienyl $(Cp)_2$ MXx complexes of transition metals.

5. The method of claim 1, 2, or 3 wherein said mediator is a phenol derivative.

6. The method of claim 4 wherein said phenol derivative is selected from the group consisting of: ferrocene-phenols; and indophenols.

7. The method of claim 6, wherein said mediator is [N-ferrocenoyl]-4-aminophenyl phosphate.

8. The method of claim 1 wherein said first enzyme is a phosphatase.

9. The method of claim 1 wherein said electrode is poised at an electrical potential higher than the redox potential of said mediator.

10. A system for detecting activity of a first enzyme in a sample, said first enzyme converting a non-mediator to a mediator, said mediator having a reduced form and an oxidized form, said system comprising:
    (a) said non-mediator which is capable of conversion by said first enzyme to said mediator;
    (b) a second enzyme which converts said mediator from said oxidized form to said reduced form;
    (c) a substrate for said second enzyme; and
    (d) an electrode and means for poising said electrode at an electrical potential which is intermediate between the redox potential of said mediator and said non-mediator, wherein said electrical potential is such that said mediator is converted from said reduced form to said oxidized form at said electrode and said non-mediator is not oxidized or reduced at said electrode.

11. The system of claim 10, said mediator being chosen from the group consisting of: metallocenes, ruthenium compounds, carboranes, conductive salts of TCNQ, haloanils, viologen, a quinone, an alkyl-substituted phenazine derivative, a bis-cyclo pentadienyl $(Cp)_2$ MXx complexes of transition metals.

12. The system of claim 10, said mediator being a phenol derivative.

13. The system of claim 12, said phenol derivative is chosen from the group consisting of: ferrocene-phenols and indophenol compounds.

14. The system of claim 13, wherein said mediator is [N-ferrocenoyl]-4-aminophenyl phosphate.

15. The system of claim 10, said first enzyme being a phosphatase.

16. The system of claim 10, wherein said electrical potential is higher than the redox potential of said mediator.

17. The system of claim 10, wherein said first enzyme is bound to an antigen or an antibody as a label.

* * * * *